(12) United States Patent  
Bouis et al.

(10) Patent No.: US 6,203,679 B1  
(45) Date of Patent: Mar. 20, 2001

(54) ELECTROPHORESIS GEL CONTAINER APPARATUS AND METHOD OF USE THEREOF

(75) Inventors: Paul A. Bouis; Steven C. Magee, both of Bethlehem, PA (US); Chien-Pin S. Hsu, Basking Ridge, NJ (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/251,129

(22) Filed: Feb. 16, 1999

Related U.S. Application Data

(60) Provisional application No. 60/074,790, filed on Feb. 16, 1998.

(51) Int. Cl.$^7$ .......................... G01N 27/26; G01N 27/447
(52) U.S. Cl. .......................... 204/466; 204/456; 204/606; 204/613; 204/616
(58) Field of Search .................. 204/606, 613, 204/616, 618, 456, 466, 465

(56) References Cited

U.S. PATENT DOCUMENTS

| | | | |
|---|---|---|---|
| 4,234,400 | * 11/1980 | Kaplan et al. | 204/461 |
| 4,415,418 | * 11/1983 | Turre et al. | 204/466 |
| 4,588,491 | * 5/1986 | Kreisher et al. | 204/620 |
| 4,652,354 | * 3/1987 | Place et al. | 204/466 |
| 4,657,655 | * 4/1987 | Smoot et al. | 204/612 |
| 4,889,610 | * 12/1989 | Flesher et al. | 204/620 |
| 4,911,816 | * 3/1990 | Love et al. | 204/614 |
| 5,443,704 | * 8/1995 | Kirkpatrick et al. | 204/620 |
| 5,514,255 | * 5/1996 | Gautsch | 204/466 X |
| 5,582,702 | * 12/1996 | Cabilly et al. | 204/456 |
| 5,785,835 | * 7/1998 | Saito et al. | 204/616 |
| 5,865,974 | * 2/1999 | Cabilly et al. | 204/456 |
| 6,036,021 | * 3/2000 | Moi | 204/456 X |

\* cited by examiner

*Primary Examiner*—Jeffrey Snay  
*Assistant Examiner*—John S. Starsiak, Jr.

(57) ABSTRACT

An electrophoresis container apparatus having (1) a primary container tray made from a UV light transmitting materials, (2) a UV light transmitting gel contained in the primary container tray, and (3) a removable top sheet for covering the gel. The removable top sheet may also be UV light transmitting. The apparatus optionally comes with a handle having pincers for grasping the primary container and permitting easy movement of the apparatus from location to location. Because the apparatus transmits UV light, the gel can be used and analyzed while it is still in the tray. This eliminates the need to remove the gel before analysis and reduces the chances that the gel will be damaged during handling. Similarly, because the apparatus has an optional handle, the user can move the apparatus form location to location without touching the apparatus and exposing the user to dangerous chemicals, e.g., those often used in staining procedures.

15 Claims, 4 Drawing Sheets

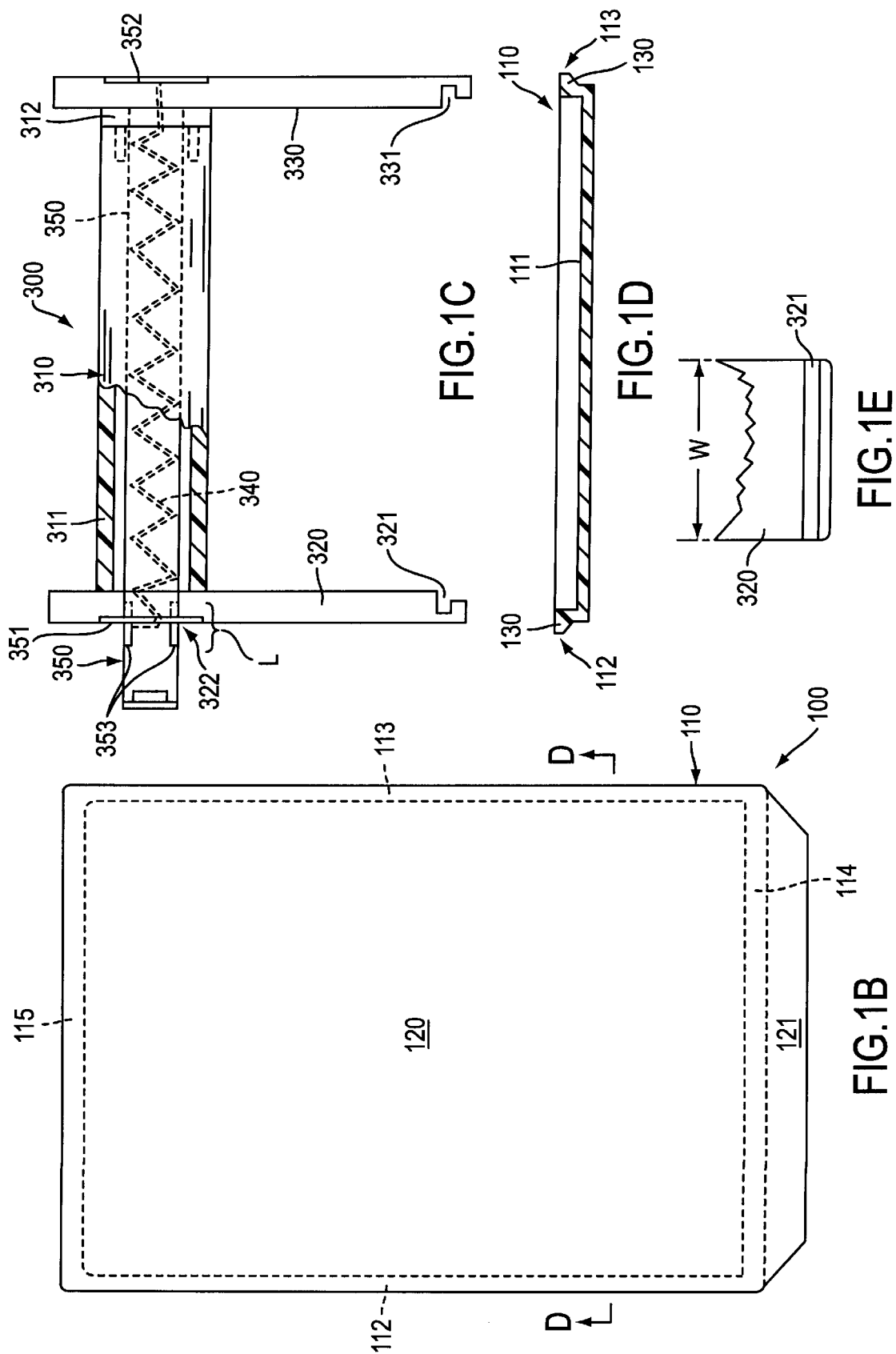

ELECTROPHORESIS GEL CONTAINER APPARATUS AND METHOD OF USE THEREOF

This is a nonprovisional application claiming benefit of provisional application 60/074,790, filed on Feb. 16, 1998.

BACKGROUND OF THE INVENTION

1. Field of the Invention

This invention relates generally to apparatuses and methods for conducting gel electrophoresis. In particular, the present invention relates to ultraviolet light transparent apparatuses for holding electrophoresis gels and to methods for using such apparatuses to simply and safely process electrophoresis gels.

2. Background of the Invention

Gel electrophoresis is widely used in the molecular biology and biotechnology fields. Initially all laboratories made their own electrophoresis gels and apparatuses for containing such gels. Subsequently, as such gels became popular they were prefabricated and sold to laboratories in compact and easy to use apparatuses. However, prefabricated electrophoresis gels for are fragile and are subject to drying. Thus, these gels must be handled carefully.

Agarose gels has also been widely used in the molecular biology and biotechnology fields. Typical procedures include preparing the agarose gel, loading samples, running the electrophoresis, staining the samples with fluorescent dyes, and photographing the gels. The use of precast or prefabricated gels eliminates the time required for gel preparation and greatly minimizes potential human contact with highly toxic fluorescent dye stains.

One known electrophoresis gel container for packaging prefabricated electrophoresis gels or to be cast electrophoresis gels is shown in U.S. Pat. No. 5,443,704, entitled "Electrophoresis Gel Container Assemblies." The device of the '704 patent has a number of drawbacks. For example, it is not transparent to sufficient ultraviolet ("UV") light to illuminate ethidium bromide-stained DNA bands. Therefore, visualization of stained bands of DNA fragments cannot be made with the '704 device while the gel is still within the gel container. With the '704 device, the user is required to remove the gel from the cassette and place the gel directly onto the ultraviolet light source (e.g., transilluminator) for viewing or photography (i.e., photographing to keep a record of the results). In contrast, according to one aspect of the invention discussed below, one can place the entire apparatus with the gel contained therein directly onto a transilluminator for direct viewing or photography.

The '704 device also does not provide an immediate means of handling the gel without user contact with various solutions used in staining and destaining. In contrast, according to another aspect of the present invention as discussed below, handles are provided that allow the user to transfer the gel and container from place to place and from solution to solution without contacting the gel. This aspect of the invention minimizes the likelihood of contamination and prevents the user from contacting dangerous solutions commonly used in staining, e.g., ethidium bromide (a mutagen used in DNA and RNA staining).

SUMMARY OF THE INVENTION

The present invention provides an improved disposable apparatus for holding electrophoresis gels. The apparatus, typically in the form of a tray, is constructed from UV light transparent materials and contains a UV light transparent pre-cast gel. The improved apparatus: (1) provides a method for conducting UV light analysis on the gel without removing the gel from the apparatus and (2) provides convenient and safe handling of gels by minimizing potential human contact with hazardous fluorescent dye stains.

According to one aspect of the invention, an electrophoresis container apparatus is provided which includes: a primary container having a bottom for supporting an electrophoresis gel and perimeter side walls extending from the bottom, the primary container being made from a UV light transmitting material; a removable top sheet adhered to the perimeter side walls of the primary container, optionally made from a UV light transmitting material; and an electrophoresis gel within the primary container, the gel being a UV light transmitting gel.

According to another aspect of the invention, a handle is provided that is configured to grasp opposite sides of the primary container. Preferably, the handle includes two opposing legs that are biased towards one another.

According to another aspect of the invention, a method of analyzing samples in an electrophoresis gel includes: a) providing an electrophoresis container apparatus, comprising: a primary container having a bottom for supporting an electrophoresis gel and perimeter side walls extending from the bottom, the primary container being made from a UV transmitting material; a removable top sheet adherable to the perimeter side walls of the primary container, optionally made from a UV light transmitting material; b) pre-casting a UV light transparent electrophoresis gel within the primary container; c) loading samples into the gel; d) carrying out electrophoresis on the samples; e) visualizing the samples in the gel with UV irradiation transmitted to the gel through the primary container. Optionally, the removable top sheet is completely removed before visualizing the samples in the gel or allowed to remain on the apparatus while visualizing the samples in the gel. If the removable top sheet is allowed to remain on the apparatus during visualization, it can be made of UV light transparent materials or, for analysis where visible light is emitted from the sample, from non-UV transparent materials. In gels where the stain is not included in the gel mixture, further steps of staining and rinsing the gel after carrying out the electrophoresis may be needed.

According to another aspect of the invention, the method also includes the step of grasping the primary container with the gel therein with a handle and transferring the container and gel to required locations during steps that require the apparatus to be moved, e.g., the visualization step requiring transfer to an illuminator or the optional staining and rinsing steps.

The above and other advantages, features and aspects of the present invention will be more readily perceived from the following description of the preferred embodiments thereof taken together with the accompanying drawings and claims.

BRIEF DESCRIPTION OF THE DRAWINGS

The present invention will become more fully understood from the detailed description given below and the accompanying drawings which are given by way of illustration only, and are not limiting of the present invention, and wherein:

FIG. 1(B) is a top view of a gel container showing the top sheet and the primary container thereunder in dashed lines;

FIG. 1(C) is a side view of a handle according to one specific embodiment, showing a portion of the base partially cut-away;

FIG. 1(D) is a cross-sectional view of the primary container taken along the line D—D shown in FIG. 1(B);

FIG. 1(E) is a side view of a section of a leg portion from the right side of FIG. 1(C);

DETAILED DESCRIPTION OF THE PREFERRED EMBODIMENTS

The preferred embodiments of the present invention comprise a UV light transparent tray containing a UV light transparent electrophoresis gel or media covered by a removable top. The apparatus is in the form of a pre-cast and pre-packaged gel in a ready-to-use tray. The present invention is preferably designed for use in electrophoretic separations of polymeric biological materials, such as DNA, RNA and proteins.

According to the present invention, the gel contained in the tray may be stained or blotted in such a way as to allow transfer or visualization without removing the gel from the apparatus. The present invention is thus safer to use with dangerous solutions than present pre-cast apparatuses available in the marketplace.

In summary, as discussed below, preferred embodiments of the present invention show a gel tray apparatus wherein:

(a) the gel tray is transparent to UV light at useful wavelengths;

(b) the gel (gel with buffer incorporated in the gel) is transparent to UV light at useful wavelengths; and/or (c) the gel tray has unique handles to facilitate use and safety.

FIGS. 1(A)–1(D) show an exemplary preferred embodiment of the invention. A container 100, FIG. 1(A), includes a primary container 110, FIG. 1(D), and a top sheet 120, FIG. 1(B). The primary container 110—or gel tray—serves as the primary holder of the gel material used for separations. The primary container 110 is preferably made from an ultraviolet ("UV") light transparent plastic. In this manner, the primary container can be placed, e.g., directly onto a transilluminator for viewing, rather than a user having to remove the contained gel therefrom.

The UV transparent plastic is preferably either polymethylpentene UV transparent ("UVT") acrylic. The preferred tray containing the gel is ultraviolet and visible light ("UV-VIS") transparent. This enables visualization while the gel is within the container. For example, a convenient method of visualizing DNA in agarose gel includes using the fluorescent dye ethidium bromide, which is a highly toxic chemical. UV irradiation absorbed by the DNA at 260 nm and transmitted to the dye, or irradiation absorbed at 300 nm and 360 nm by the bound dye itself is emitted at 590 nm in the red-orange region of visible spectrum.

The material used for the primary container 110 and the top sheet 120 is preferably sufficiently UV transparent that enough UV light penetrates the primary container to strike the DNA bands in the gel to give substantial radiation in the visible wavelengths. Tests conducted with a variety of plastics indicate that only select materials such as polymethylpentene and UVT acrylic are sufficiently UV transparent to allow enough UV light to penetrate for good band visualization in, for example, observing DNA fragments with ethidium bromide staining.

Figure 1A:
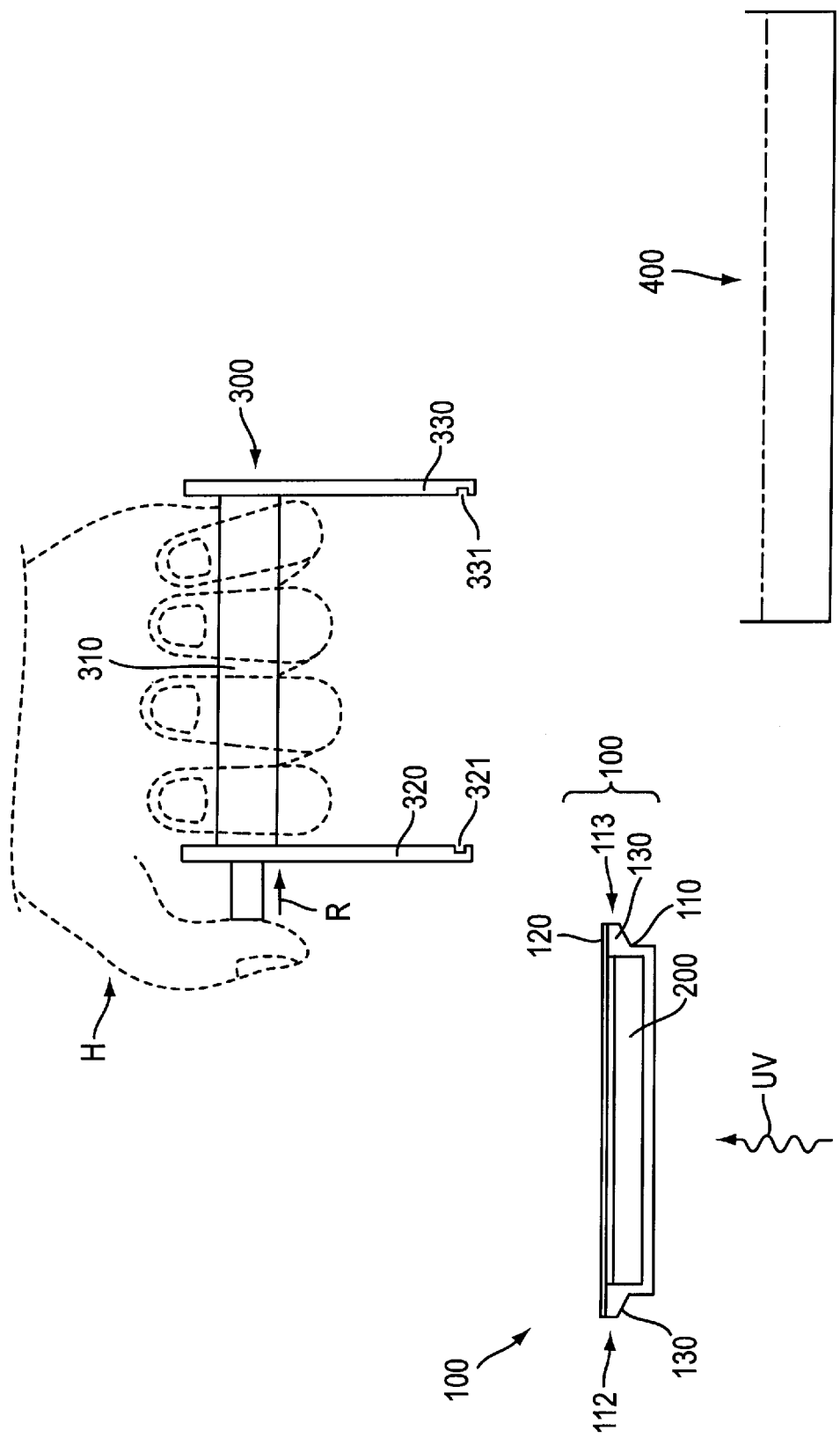
FIG. 1(A) is a schematic side view showing one embodiment with a gel container, a handle held by a user and a solution into which the gel container may be placed.

The top sheet 120 is adhered to the primary container—e.g., with an adhesive—so as to form an envelope which holds the gel 200, FIG. 1(A), in a sufficiently rigid configuration as to be useable when desired. The primary container 110 preferably has an inner surface 111 that is adapted to provide good adherence of the gel 200 thereto. Pre-treatments for common plastic materials that allow good adherence of the gel to the plastic are desirable. For example, plastics with a rough ("buffed") finish can allow good adherence of the gel to the plastic so as to avoid premature release of the gel from the cassette.

Preferably, the primary container 110 is also sufficiently sturdy to allow pressure to be imparted on opposite sides thereof, e.g., at side walls 112 and 113, to allow the container 110 to be handled. The primary container 110 preferably has a sufficient strength to allow a user to lift the container with a pincer or a handle 300, discussed below, without bending the container and damaging the gel contained therein. It can be important to provide the handles with sufficient inherent strength to grasp the primary container with the gel intact so as to allow handling without concern for damage or loss. It may also be important that the material used for the primary container 110 (and the top sheet 120 of the gel container) should also be rigid enough to support and maintain the integrity of the gel in transit to customers, even in transit to foreign countries, but flexible enough to allow easy removable.

The top sheet 120 of the container also preferably aids in maintaining a flat upper surface on the gel 200 and in protecting the gel 200 and the wells formed therein from being scratched or marred which would reduce the utility in the visualization of the bands. The top sheet 120 also protects the gel 200 from the evaporation of water in the buffer, The top sheet 120 is preferably made of plastic or, alternatively, of a water-impenetrable membrane of some sort.

As noted, the device preferably includes at least one handle 300. Preferably, only one handle is provided, however, more than one handle can be provided. The handle 300 is preferably constructed to allow a user to move the primary container 110 and the gel 200 therein into, through, and from any solution (e.g., shown schematically in FIG. 1(A) at 400) which could be dangerous were the user to come in contact with this solution. The handle 300 preferably allows the user to grasp, lift, and move the gel container 110 without directly contacting the gel container 110, the gel 200, or the solutions, e.g. 400, used in the gel's normal use and band visualization.

The handle is preferably be made of plastic, metal, and/or wood. The handle can also be made to have sufficient strength to be used to submerge the gel container completely in an electrophoresis, a staining, or a washing medium and to allow the user to move the container and gel about freely. In addition, the handle 300 is preferably attachable to and detachable from the primary container 110.

According to one embodiment, the handle has a generally upside-down "U" shape. A base portion 310 of the "U" shape is preferably adapted to be grasped by a user's hand H, and the legs 320, 330 are preferably adapted to engage opposite sides 112, 113 of the primary container 110. In order to facilitate engagement of the legs 320, 330 with the primary container 110, the legs 320, 330 can include grooves 321, 331 cut into their grasping ends so as to allow an edge or flange 130 of the primary container 110 to nest neatly therein, to provide a sure and tight fit. The legs 320, 330 are preferably biased with a biasing means, such as a spring, towards one another so as to firmly engage the opposite sides of the primary container. As shown in FIG. 1(C), one preferred embodiment of the biasing means includes a coil spring 340 which is fixedly connected to an upper side of both legs under tension therebetween. That is, the base of the "U" preferably has a spring-loaded device that draws the leg portions of the "U" together. Preferably, the spring-loaded device can release the gel container when pressure is applied by the user to create a bias opposite to that of the spring.

In the preferred embodiment shown in FIG. 1(C), the base 310 is formed from a hollow tube 311. The hollow tube 311 is fixedly attached to the upper end of the leg 320 with adhesives or the like. The leg 320 has a circular hole 322 formed therein that snugly receives a central hollow tube 350. The tube 350 extends through the center of the hollow tube 311 and is fixedly attached at an opposite end thereof to the leg 330. As a result, the tubes 350 and 311 are each fixed to respective ones of the legs and can be moved relative to one another in a telescoping manner. If desired, a plug member 312 can be fitted in the end of the tube 311 to provide a contact surface for the upper end of the leg 330 and to provide a snug opening therethough for the tube 350. As shown, the plug member 312 has an inner portion 313 received in the end of the tube 311 and a central opening through which the tube 350 extends. The opposite end of the tube 350 extends out past the leg 320 such that it can be pressed in the direction R, FIG. 1(A), to expand or separate the legs 320, 330. The coil spring can be fixed, for example, to pins 351, 352 which are fixed to the legs 320, 330, respectively. Preferably, a keyway is provided between the telescoping parts to prevent the legs 320, 330 from rotating relative to one another about the central axes of the tubes 311, 350. In the illustrated embodiment, the pin 351 extends through upper and lower elongated slots 353 extending axially along the tube 350 such that the pin 351 is snugly received therein and passes therethrough. The length L of the slots 353 preferably limits outward movement of the leg portions, while the width of the slots limits rotational movement as discussed. Although this exemplary embodiment has been described in detail, it should be understood that the handle 300 can be modified in a variety of ways as would be understood by those in the art based on this disclosure.

FIG. 1(E) shows a side view of the leg 320 from the right side in FIG. 1(C). The leg 330 is preferably similar. The legs 320, 330 preferably have a width W that can extend along the sides 112 and 113 of the primary container to stably support the container when grasped. In one exemplary construction, the size of the width W relative to the length of the container 110 can be approximately as shown in FIGS. 1(E) and 1(B).

An important parameter of the preferred gel 200 is to have the gel transparent to UV light at useful wavelengths. Increased gel transparency can be obtained by the inclusion of certain modified polysaccharides (e.g., J.T. Baker's GelTwin and/or GelTwin II).

The gel 200 formed within the gel container is preferably made of agarose, an agarose + GelTwin II (J.T. Baker, catalog # 4370) combination, acrylamide, polyacrylamide, polyacrylamide analogues, natural polysaccharides, modified polysaccharides, or some combination thereof. The gel may contain a buffer and/or pre-staining agent or staining agent commonly used in the visualization of large polymers. The buffer is typically selected from any one of the commonly used buffers for DNA electrophoresis, such as TAE (Tris-Acetic Acid-EDTA), TBE (Tris-Boric Acid-EDTA) or TPE (Tris-Phosphoric Acid-EDTA) or protein electrophoresis, such as Tris-chloride or Tricine. The gel 200 is most preferably made of about 0.5–8% agarose. The gel 200 may have wells W shown in FIG. 3 pre-set therein so that it is ready for sample application and use upon removing the top sheet 120 of the two-part container.

Figure 2A:
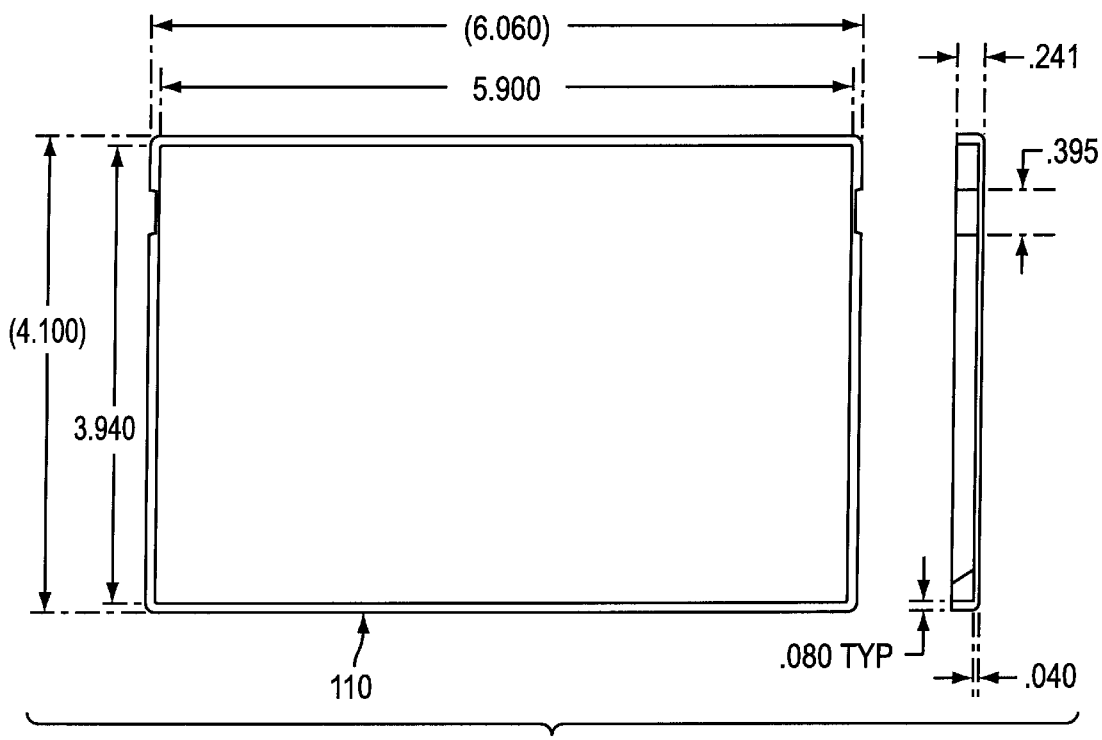
FIG. 2(A) is a top and side view of a primary container according to one exemplary construction.
Figure 2B:
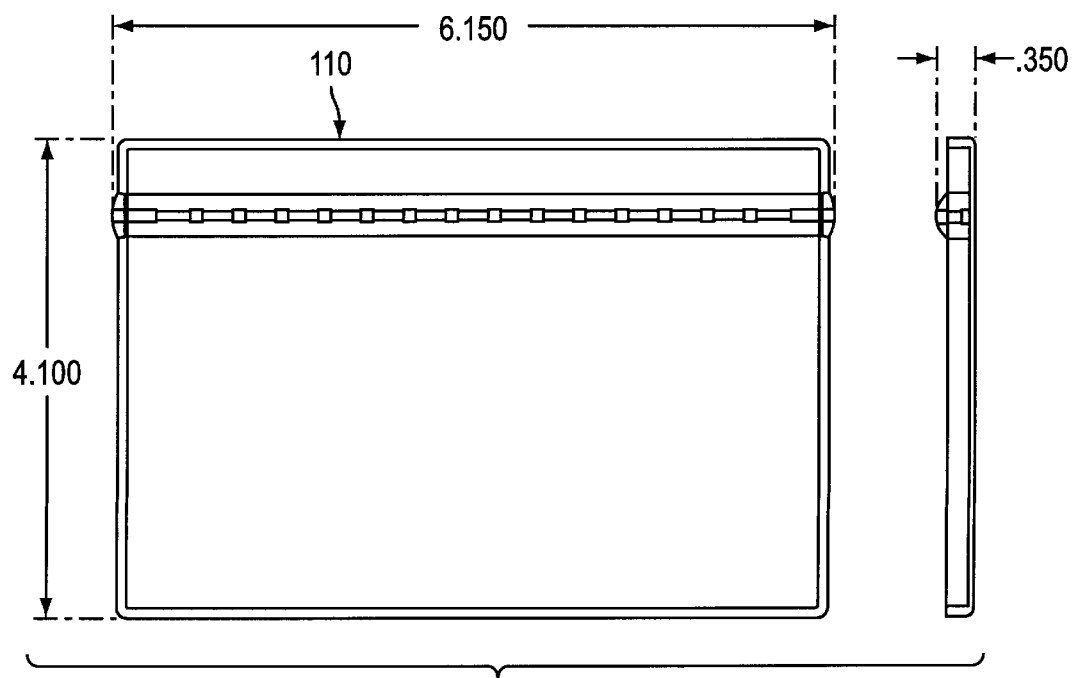
FIG. 2(B) is a top and side view of a primary container and a comb therein according to one exemplary construction.
Figure 3:
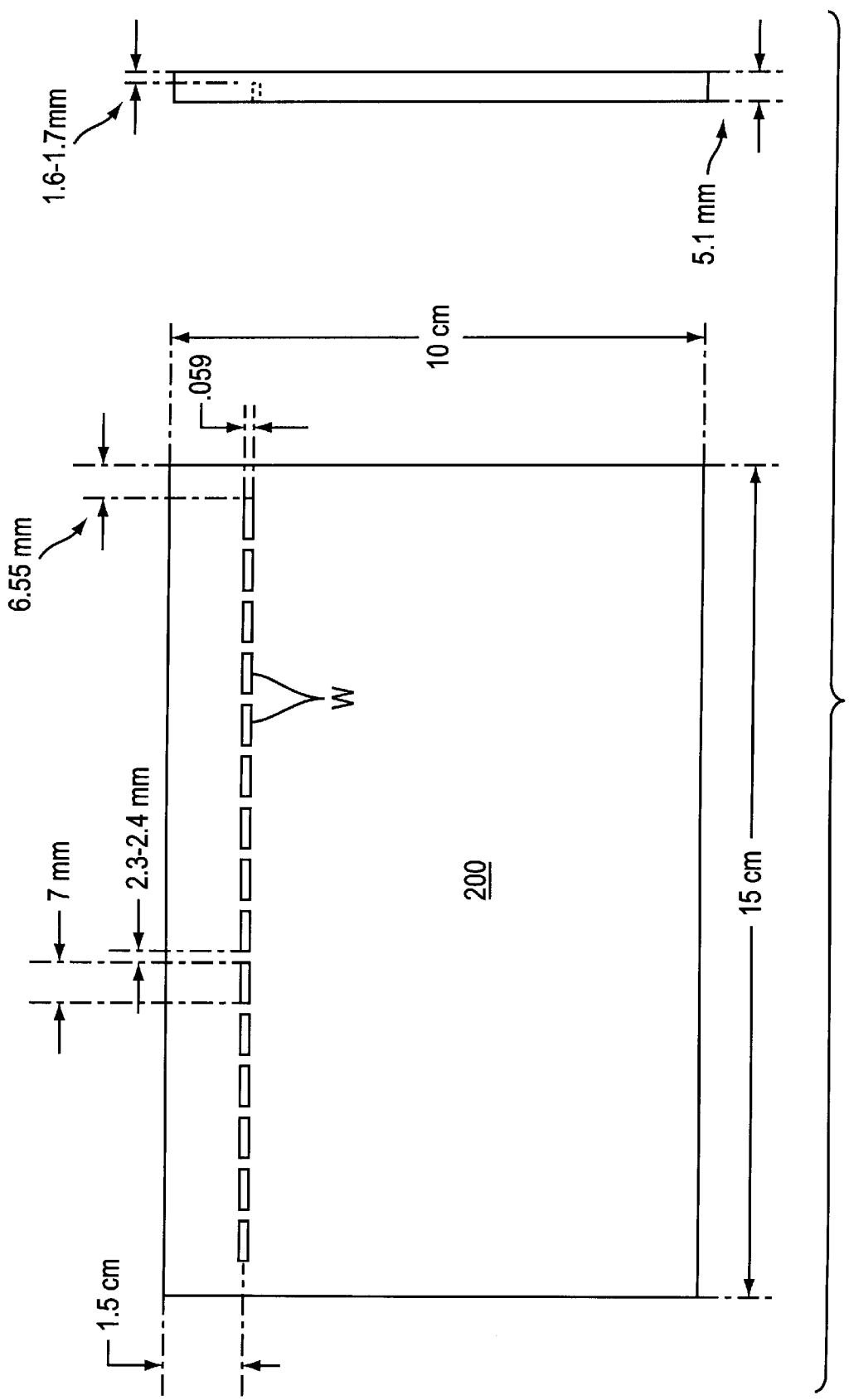
FIG. 3 is a top and side view of gel dimensions according to one exemplary construction.

FIGS. 2(A) and 2(B) illustrate dimensions of a container 110 according to one exemplary embodiment. FIG. 3 illustrates sizes of the gel 200 within the primary container according to one exemplary embodiment. In FIGS. 2–3, the reference numerals shown between arrows are also the sizes thereof in inches, except where the letters "cm" or "mm" are included, wherein such represent centimeters or millimeters, respectively. Dimensions described in the present disclosure fit a few of the more popular units, but are not necessarily ideal for all commercial submarine gel electrophoresis chambers. Those skilled in the art would recognize how to adapt the present invention to the particular application at hand based on this disclosure.

In the example shown in FIG. 1(B), the primary container 110 (shown in dotted lines below the top sheet 120) has a square-shape or rectangular-shape base sheet of molded UV transparent plastic with four side walls 112, 113, 114 and 115. The side walls preferably include a flange portion 130 having a generally flat upper surface for adhering the top sheet 120 thereto. Although the top sheet can be adhered to the primary container in a variety of ways, the preferred methods for adhering the top sheet include applying adhesives or glues or heat-sealing. Other methods can include, for example, applying a two-sided adhesive tape.

As noted, the top sheet 120 is preferably constructed of a UV transparent plastic but can be made from any material. The primary container 110 and the top sheet 120 together can form an envelope into which a gel-forming substance may be poured and allowed to solidify within the envelope. Alternatively, the gel may be poured in liquid form into the primary container 110 and at a later time, the top sheet 120 may be added.

When needed, the upper surface of the gel may be exposed by grasping a tab extension 121, FIG. 1(B), of the top sheet 120 and gently pulling the tab back so as to separate the top sheet 120 from the primary container 110 and from the upper gel surface to reveal the wells W of FIG. 3 previously formed by the teeth of a comb. The tab 121 can be formed, for example, by extending a portion of the top sheet 120 past an edge of the top sheet 120 adhered to the primary container.

The pre-formed wells W of FIG. 3 are preferably placed in a location in the gel allowing a good flow of electric current through the gel without interference from the walls of the primary container to distort any of the bands being electrophoresed through the gel. It can be important to place the wells designed to receive the user's samples at sufficient distances from the respective side walls of the primary container to avoid interference from these walls in the flow of electrons through the gel in a linear fashion. Based on tests conducted, the wells are preferably at a minimum of 1.0 cm from the nearest adjacent side wall, and preferably at least 1.5 cm in order to obtain bands of electrophoresed product of the highest integrity. Wells placed too close to the walls give skewed bands.

The gel container may be immersed into buffer in a submarine-style gel electrophoresis chamber commonly used in the art of submarine gel electrophoresis. Samples of the user's preference containing any of numerous natural or contrived polymeric molecules, either containing a prestaining agent or without such an agent, and containing a non-ionic agent to increase the density of the solution such as to cause the sample to sink into the wells may then be applied to the wells.

The power supply may then be connected via the leads supplied by the manufacturer. The current can then be turned on for an extent and time sufficient for the migration of the molecules far enough in the gels to be satisfactory for the purposes of the user. In some situations, the bands may be viewed during electrophoresis as they progress through the gel medium by irradiating them with certain visible or ultraviolet light.

At an appropriate point, the current may be disconnected and the gel removed from the electrophoresis chamber and viewed directly, transferred to a visible or ultraviolet light illuminating table such as is commonly used in the visualization and/or photography of gels in the art of electrophoresis visualization and photography, or transferred with the aid of the handle to a solution containing a staining agent appropriate for the user's needs, such as ethidium bromide, for the visualization of DNA bands on the gel. Should the user choose to transfer the container to a staining solution, which typically will contain agents which the user would find dangerous, the handle 300 for the container will allow the user to avoid direct contact with the solution by using these handles for any grasping and moving necessary to place the container and gel combination into the solution or to remove it from the solution. Any desired agitation while in these solutions may be carried out by manual movement of the container via the handle or by placing the container of the solution and the container onto a platform which can be moved to cause agitation of the solution sufficient across the surface of the gel—e.g., to wash to and fro—but not vigorous enough to splash about freely and thus above the surface of the solution. At the conclusion of this staining period, the user may remove the container and gel via the handles without directly contacting the staining solution nor damaging the gel or its contents. The container and gel may then be placed in a washing solution in the same manner as in the staining process so as to remove excess staining solution or to further enhance the sensitivity of the staining process. The container and gel can then be placed onto an illumination table as described above for the purpose of visualization or photography. Visualization or photography may be carried out in a manner as known in the art of photography of electrophoresis gels.

At the conclusion of the visualization or the photography process, the gel container and the gel may be discarded according to normal laboratory practices. The gel can also be removed from the gel container, such as with a common laboratory spatula. In addition, the gel could be further treated—e.g., with a second staining agent—or dried or stored for later reference.

The invention being thus described, it will be apparent to those skilled in the art that the same may be varied in many ways without departing from the spirit and scope of the invention. Any and all such modifications are intended to be included within the scope of the following claims.

What is claimed is:

1. A gel electrophoresis container apparatus comprising:
   a primary container having a bottom for supporting an electrophoresis gel and perimeter side walls extending from said bottom, said primary container being made from a ultraviolet light transmitting material;
   a removable top sheet adhered to said perimeter side walls of said primary container;
   an electrophoresis gel within said primary container, said gel being a ultraviolet light transmitting gel; and
   a handle configured to grasp opposite sides of said primary container.

2. The apparatus according to claim 1, wherein said top sheet is made from a ultraviolet light transmitting material.

3. The apparatus according to claim 1, wherein said handle includes two opposing legs that are biased towards one another.

4. The apparatus according to claim 1, wherein at least a portion of said primary container is a material selected from the group consisting of polymethylpentene and ultraviolet light transmitting acrylic.

5. The apparatus according to claim 1, wherein said gel is selected from the group consisting of agarose, acrylamide, polyacrylamide, polyacrylamide analogues, natural polysaccharides, modified polysaccharides, or combinations thereof.

6. The apparatus according to claim 1, wherein said gel is an agarose gel.

7. The apparatus according to claim 6, wherein said gel contains a 0.5–8% agarose gel.

8. The apparatus according to claim 1, wherein said gel contains agarose and modified polysaccharide.

9. The apparatus according to claim 1, wherein said gel contains a buffer.

10. The apparatus according to claim 1, wherein said gel contains a staining agent.

11. A method of analyzing samples in an electrophoresis gel, comprising the steps of:
    a) providing a gel electrophoresis container apparatus, comprising:
       a primary container having a bottom for supporting an electrophoresis gel and perimeter side walls extending from said bottom, said primary container being made from a ultraviolet light transmitting material;
       a removable top sheet adherable to said perimeter side walls of said primary container;
    b) an electrophoresis gel within said primary container, said gel being a ultraviolet light transmitting gel;
    c) loading samples into said gel;
    d) carrying out electrophoresis on said samples;
    e) visualizing the samples in the gel with ultraviolet light transmitted to said gel through said primary container; and
    f) grasping the primary container with the gel therein with a handle and transferring the container and gel to another location.

12. The method of claim 11, further comprising the step of staining said gel after completion of step d).

13. The method of claim 12, further comprising the step of rinsing said gel after staining said gel.

14. The method of claim 11, further comprising the step of grasping the primary container with the gel therein with a handle and transferring the container and gel to an illuminator for carrying out said step e).

15. The method of claim 11, wherein said step of grasping the primary container with the gel therein with a handle and transferring the container and gel to another location includes transferring the container and gel to a solution containing a staining agent.

* * * * *